United States Patent [19]

Szantay et al.

[11] 4,193,998
[45] Mar. 18, 1980

[54] 1,2,3,4,6,7-HEXAHYDRO-11BαH-BENZO[A]-QUINOLIZINE-DERIVATIVES

[75] Inventors: Csaba Szántay; Lajos Szabó; István Tóth; Erzsébet Kanyó; Gyula Sebestyén; Sandor Virág, all of Budapest, Hungary

[73] Assignee: Chinoin Gyogyszer es Vegyeszeti Termekek Gyara RT, Budapest, Hungary

[21] Appl. No.: 915,379

[22] Filed: Jun. 14, 1978

[30] Foreign Application Priority Data

Jun. 15, 1977 [HU] Hungary ............................. CI 1751

[51] Int. Cl.² ..................... A61K 31/47; C07D 455/06
[52] U.S. Cl. ........................................ 424/258; 546/95
[58] Field of Search ................ 424/258; 260/283 CN, 260/287 CF; 546/95

[56] References Cited

U.S. PATENT DOCUMENTS

| | | | |
|---|---|---|---|
| 3,053,845 | 9/1962 | Tretter | 260/287 CF |
| 3,634,431 | 1/1972 | Van Dyke | 260/287 CF |
| 4,102,886 | 7/1978 | Szantay et al. | 546/95 |
| 4,133,812 | 1/1979 | Szantay et al. | 546/95 |

OTHER PUBLICATIONS

March, "Advanced Organic Chemistry," (1968), pp. 318–321 and 678–679.

*Primary Examiner*—David Wheeler
*Attorney, Agent, or Firm*—Karl F. Ross

[57] ABSTRACT

There are provided new compounds of the formula I

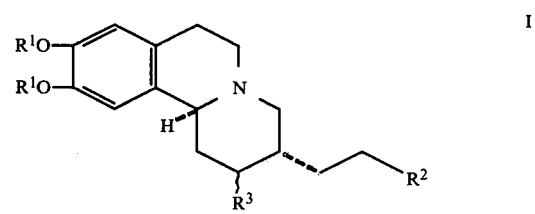

wherein
both $R^1$ moieties stand for an alkyl group having 1 to 4 carbon atoms or form together a methylene bridge,
$R^2$ is cyano or an alkoxycarbonyl group having 1 to 4 carbon atoms in the alkoxy position,
$R^3$ is hydroxy or alkanoyloxy having 1 to 4 carbon atoms in the alkoxy position in α-position or β-steric position, and acid addition salts thereof. There is also provided a process for the preparation of the compounds of the formula I.

5 Claims, No Drawings

1,2,3,4,6,7-HEXAHYDRO-11BαH-BENZO[A]-QUINOLIZINE-DERIVATIVES

According to this invention there are provided new compounds of the formula I

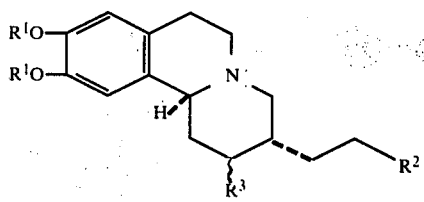

wherein
$R^1$ is alkyl containing 1 to 4 carbon atoms or the two $R^1$ moieties form together a methylene group,
$R^2$ is cyano or an alkoxycarbonyl of 1 to 4 carbon atoms,
$R^3$ is hydroxy or alkanoyloxy of 1 to 4 carbon atoms in α- or β-steric position,
and acid addition salts thereof.

There is also provided a process for the preparation of the compounds of the formula I.

The new benzoquinolizine derivatives of the formula I of the invention exhibit antiinflammatory, analgesic and gastric-juice-secretion-inhibiting activity and as such are useful as active ingredients of pharmaceutical compositions.

The benzoquinolizine compounds of the formula I are new compounds the preparation of which comprises of reducing the oxo group of the known benzoquinolizine derivatives of formula II

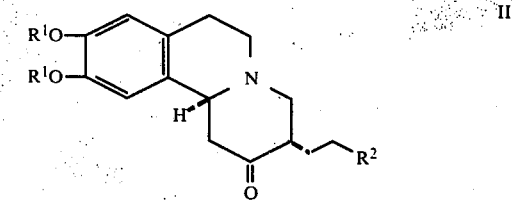

containing an oxo group in the 2-position (Hungarian Patent Specifications Nos.: 153 695 and 155 959) and acylating, if desired, the hydroxy group of the obtained compounds of formula I containing a hydroxy group in the 2-position. The compounds of the formula I can be converted to their acid-addition salts by reducing the compounds of formula I with organic and inorganic acids.

As during the reduction of the oxo group in the 2-position a chiral carbon atom is formed, the reduction results in two epimers: the 2α- and the 2β-hydroxy derivatives.

According to the invention the oxo group may be reduced by catalytically activated hydrogen and by chemical reducing agents as well.

Where the reduction is carried out by sodium borohydride, the two possible epimers are formed in different quantities. It is presumed that the hydroxy group in the 2-position of the epimer formed in a larger quantity is in β-position as this position is a more stable equatorial position from a thermodynamic point of view.

The compounds of the formula I obtained by reduction containing hydroxy in the place of $R^3$ may be acylated by the usual acylating techniques to form compounds of the formula I containing acyloxy in the place of $R^3$. The acylation is preferably conducted with acid anhydrides, mixed anhydrides or acid halogenides, such as acid chlorides of alkanoic acids containing 1 to 4 carbon atoms.

The activity of the compounds of the invention is demonstrated by the test results of the following compounds:

2α-hydroxy-3α-(2-cyano-ethyl)-9,10-dimethoxy-1,2,3,4,6,7-hexahydro-11bαH-benzo[a]quinolizine-hydrochloride (Sc-TN-1), 2α-hydroxy-3α-(2-cyanoethyl)-9,10-diethoxy-1,2,3,4,6,7-hexahydro-11bαH-benzo[a]quinolizine-hydrochloride (Sc-TN-2), 2-hydroxy-3α-(2-cyanoethyl)-9,10-methylenedioxy-1,2,3,4,6,7-hexahydro-11bαH-benzo[a]quinolizine-hydrochloride (Sc-TN-11).

The anti-inflammatory effect was tested by carrageenin and serotonine oedema of foot tests in rats. The compounds were administered per os, in the form of a suspension with 1% methyl cellulose, 1 hour prior to the injection of the inflammation-inducing agent. The activity of the compounds was determined on the basis of the difference of the foot diameter increase of the control and treated animals measured on the same day and the increase was expressed in %. The significance was tested by Student "t" test. The obtained results are included in Tables I and II.

The analgesic effect was tested in female mice by the contact heat method according to Herr-Pórszász. The compounds were administered per os in the form of a suspension prepared with a 1% methyl cellulose solution. The pain reaction time was measured 1 and 2 hours before and after the treatment. The activity was calculated by comparing the value before treatment and the measured reaction time. The prolongation of the reaction time was expressed in %. The obtained results are shown in Table III.

Table I

| Substance | Dose mg/kg | (Carrageenin) Number of animals control/treated | Activity % 1.5 h | 3 h | 4.5 h |
|---|---|---|---|---|---|
| SC-TN-1 | 100 | 10/10 | 68.9··· | 60.6··· | 33.1··· |
|  | 50 | 20/20 | 40.1``` | 29.1··· | 21.1·· |
|  | 25 | 20/20 | 25.9·· | 11.5 | 5.4 |
| SC-TN-2 | 100 | 10/10 | 48.3··· | 46.9··· | 23.3· |
|  | 50 | 20/20 | 43.4··· | 36.9··· | 20.1· |
|  | 25 | 20/20 | 23.6·· | 17.1 | — |
| SC-TN-11 | 50 | 20/20 | 45.2··· | 34.6··· | 15.5 |
|  | 25 | 10/10 | 25.2·· | 26.9··· | 19.6· |
| Indomethacin | 10 | 20/20 | 26.7·· | 36.1··· | 25.1[33]·· |
| Phenyl- | 100 | 10/10 | 32.6·· | 31.6·· | 28.9··· |
| butazone | 50 | 10/10 | 26.5·· | 22.6·· | 20.6 |

Table I-continued

| | | (Carrageenin) | | | |
|---|---|---|---|---|---|
| | Dose | Number of animals | | Activity % | |
| Substance | mg/kg | control/treated | 1.5 h | 3 h | 4.5 h |
| Na.sal. | 200 | 10/10 | 29.8ˣˣˣ | 22.3ˣˣ | 17.2 |

Table II

| | | (Serotonine) | | | |
|---|---|---|---|---|---|
| | Dose | Number of animals | | Activity % | |
| Substance | mg/kg | control/treated | 0.5 h | 1 h | 2 h |
| SC-TN-1 | 50 | 20/20 | 47.2ˣˣˣ | 43.3ˣˣˣ | 36.5ˣˣˣ |
| | 25 | 20/20 | 27.3ˣˣˣ | 30.5ˣˣˣ | 20.3ˣ |
| | 10 | 10/10 | 15.6 | 12.9 | 11.8 |
| SC-TN-2 | 50 | 10/10 | 29.5ˣˣˣ | 35.5ˣˣˣ | 26.1ˣˣˣ |
| | 25 | 20/20 | 24.4ˣˣˣ | 21.8ˣˣ | 18.2 |
| | 10 | 10/10 | 22.3ˣˣ | 19.4ˣˣ | 16.7 |
| SC-TN-11 | 50 | 20/20 | 45.4ˣˣˣ | 48.9ˣˣˣ | 45.5ˣˣˣ |
| | 25 | 10/10 | 31.1ˣˣˣ | 42.7ˣˣˣ | 37.4ˣˣˣ |
| | 25 | 10/10 | 5.6 | 1.4 | 1.6 |
| | 100 | 20/20 | 16.1 | 10.2 | 12.6 |

Table I refers to carragenine-, and Table II to serotonine oedema inhibition. The abbreviations and symbols used in the Tables are as follows:

```
Na-sal. = sodium salicylate
xxx = p < 0.001
xx  = p < 0.01
x   = p < 0.05
```

Table III

| | (Analgesic Reaction Time) | | | |
|---|---|---|---|---|
| | Dose | | Activity % | |
| Substance | mg/kg | Number of animals | 1 h | 2 h |
| SC-TN-1 | 100 | 20 | 42.2 | 29.6 |
| | 50 | 20 | 39.7 | 29.7 |
| SC-TN-2 | 100 | 20 | 33.6 | 24.6 |
| | 50 | 20 | 26.9 | 35.9 |

EXAMPLE 1

2β-Hydroxy-3α-(2-cyanoethyl)-9,10-dimethoxy-1,2,3,4,6,7-hexahydro-11baH-benzo[a]quinolizine 10 g. (31.8 mmoles) of 2-oxo-3α-(2-cyanoethyl)-9,10-dimethoxy-1,2,3,4,6,7-hexahydro-11baH-benzo[a]-quinolizine are suspended in 120 ml. of absolute methanol and 1.20 g. (31.8 mmoles) of sodium borohydride are added at 0° C. in portions under stirring. After adding all of the reducing agent the reaction mixture is stirred for an hour at room temperature. The precipitated mixture is filtered. 4.5 g. (44%) of the title compound is obtained. (A further 1.1 g. of solid is precipitated from the mother liquor and the total yield amounts to 55%). If the filtered solid also contains the other isomer, the product is purified by recrystallization from methanol.

M.p.: 160° C. The hydrochloride salt melts at 234° C.

Analysis for the formula $C_{18}H_{24}N_2O_3$ (molecular weight: 316.39) calculated: C %: 68.32; H %: 7.64; N %: 8.856; found: C %: 68.03; H %: 7.65; N %: 8.97.

IR spectrum (KBr): at 3100 (—OH); 2310 (—CN); 1100 [C—O(H)] cm$^{-1}$.

Mass spectrum: (M)e,%): 316 (100); 317 (86.7); 300 (16.3); 272 (562); 233 (67.5); 205 (74.3); 191 (60.2).

EXAMPLE 2

2α-Hydroxy-3α-(2-cyanoethyl)-9,10-dimethoxy-1,2,3,4,6,7-hexahydro-11baH-benzo[a]quinolizine 0.5 g. of the mother liquor obtained after the separation of the 2β-hydroxy derivative according to the previous Example is subjected to thin layer chromatography on a plate KG-PF$_{254-366}$, developed with a 14:3 benzene-methanol system and 2α-hydroxy compound is obtained.

Yield: 120 mg. 23 %. The R$_f$ value of the 2α-hydroxy derivative is greater than that of the 2β-hydroxy derivative.

M.p.: 145° C.

IR spectrum (KBr): at 3350 (—OH); 2300 (—C≡N); 1065 (C—O(H)) cm$^{-1}$.

Mass spectrum (M)e,%): 316 (M+, 35); 276 (100); 218 (24); 205 (18); 191 (22).

EXAMPLE 3

2β-Acetoxy-3α-(2-cyanoethyl)-9,10-dimethoxy-1,2,3,4,6,7-hexahydro-11baH-benzo[a]quinolizine 1.14 g. (3.60 mmoles) of 2β-hydroxy derivative prepared according to Example 1. is dissolved in 15 ml. of a 1:1 mixture of acetic acid anhydride and pyridine and the mixture is allowed to stand at room temperature for 24 hours. The reaction mixture is evaporated in vacuum and the residue is taken up in a small amount of water and alkalized with saturated ammonium hydroxide solution to pH=8. 1.2 g. of the named compound is obtained (95%). The solid is purified by recrystallization from methanol.

M.p.: 122° C. The hydrochloride salt is decomposed from 235° C.

Analysis for the formula $C_{20}H_{26}N_2O_4$ (molecular weight: 358.54): calculated: C %: 60.80; H %: 7.14; N %: 7.08; found: C%: 60.92; H %: 7.24; N %: 7.20.

IR spectrum (KBr): 2780 (Bohlmann band): at 2320 (—−−−N); 1750 (—C=O); 1230–1250 (C—O—C$_{as}$); 1040 (C—O—C$_s$) cm$^{-1}$.

Mass spectrum (M)e,%): 360 (M+2)+, 9.0); 359 (M+1)+, 48); 358 (M+, 35); 316 (4); 300 (100); 298 (23); 272 (30); 247 (19); 233 (18); 206 (33).

NMR spectrum (in deutero-chloroform): δ=6.74 and 6.67 (2H, s, aromatic protons); at 5.15 (1H,m,

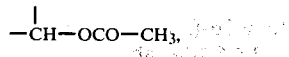

τ=24 Hz); 4.14 (6H, s, —OCH₃); 2.12 (3H, s, —OCO—CH₃) ppm.

EXAMPLE 4

2α-Acetoxy-3α-(2-cyanoethyl)-9,10-dimethoxy-1,2,3,4,6,7-hexahydro-11baH-benzo[a]quinolizine 0.20 g. (0.63 mmoles) of 2α-hydroxy derivative prepared according to Example 2. is dissolved in 5 ml. of a 1:1 mixture of pyridine and acetic acid anhydride and the solution is allowed to stand at room temperature for one day. The mixture is poured on a small amount of ice whereafter the pH is adjusted to 8 by the addition of saturated ammonium hydroxide solution. The precipitated solid is filtered and washed with methanol. 160 mg. (70%) of the title compound is obtained.

M.p.: 148°-149° C.

IR spectrum (KBr): at 2300 (—C⁻⁻—N);

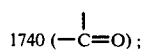

1230-1260 (C—O—C$_{as}$) cm⁻¹.

Analysis for the formula C₂₀H₂₆N₂O₄ (molecular weight: 358.45): calculated: C %: 60.80; H %: 7.14; N %: 7.08; found: C %: 60.94; H %: 7.32; N %: 7.34.

Mass spectrum )M(e,%): 358 (M⁺, 17); 319 (3); 301 (20); 300 (100); 206 (9); 191 (6).

NMR spectrum (in deutero-chloroform): at δ=6.63 (2H, s, aromatic protons); 4.78 (1H,m,

3.68 (6H, s, —OCH₃); 2.15 (3H, s, —OCO—CH₃) ppm.

EXAMPLE 5

2β-Hydroxy-3α-(2-cyanoethyl)-9,10-diethoxy-1,2,3,4,6,7-hexahydro-11baH-benzo[a]quinolizine 10.0 g. (29.2 mmoles) of 2-oxo-3α-(2-cyanoethyl)-9,10-diethoxy-1,2,3,4,6,7-hexahydro-11baH-benzo[a]quinolizine is dissolved in 150 ml. of absolute methanol. 1.1 g. (29.2 mmoles) of sodium borohydride is added at 0° C. under stirring. After completing the addition the reaction mixture is stirred at room temperature for half an hour. The solution is neutralized with a small amount of acetic acid and evaporated in vacuum. The residue is taken up in a water, alkalized with a saturated ammonium hydroxide solution, extracted with dichloromethane and after drying with anhydrous magnesium sulfate the organic layer is evaporated in vacuum. 9.48 g. of residue is recrystallized from ethanol. 4.77 g. (47.5%) of the title compound is obtained. Upon standing a further 2 g. (20%) of the title compound is precipitated from the mother liquor. The total yield amounts to 6.77 g. (67.5%).

M.p.: 136° C. The hydrochloride melts at 210° C.

Analysis for the formula C₂₀H₂₈N₂O₃ (moleclar weight: 344.44): calculated: C %: 69.80; H %: 8.20; N %: 8.70; found: C %: 69.50; H %: 8.16; N %: 8.33.

IR spectrum (KBr): at 3100 (—OH); 2770 (Bohlmann band): 2270 (—C⁻⁻—N); 1040 (CO(H)) cm¹.

EXAMPLE 6

2β-Acetoxy-3α-(2-cyanoethyl)9,10-diethoxy-1,2,3,4,6,7-hexahydro-11baH-benzo[a]quinolizine 1.0 g. (2.9 mmoles) of the 2β-hydroxy derivative prepared according to the Example 5. is dissolved in 15 ml. of a 1:1 mixture of pyridine and acetic acid anhydride. The reaction mixture is allowed to stand at room temperature for 24 hours, the mixture is evaporated in vacuum whereafter the residue is triturated with a small amount of water and alkalized with a saturated ammonium hydroxide solution. 750 mg. (67%) of the title compound is precipitated. The product is recrystallized from methanol.

M.p. 99°-102° C. Melting point of the hydrochloride salt is 245° C.

Analysis for the formula C₂₂H₃₀N₂O₄.HCl (molecular weight: 423.05): calculated: C %: 62.48; H %: 7.39; N %: 6.63; found: C %: 62.62; H %: 7.70; N %: 6.93.

IR spectrum (KBr): 2720 (Bohlmann band); 2300 (—C⁻⁻—N);

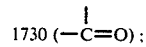

1230-1240 (C—O—C$_{as}$): 1020 (C—O—C$_s$) cm⁻¹.

NMR spectrum (in deutero-chloroform): δ=6.68 and 6.64 (2H, s, aromatic protons); at 4.74 (1H, m,

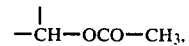

τ=24 Hz); 4.18-4.92 (4H, q, —OCH₂—) ppm.

EXAMPLE 7

2β-Hydroxy-3α-(2-methoxycarbonyl-ethyl)-9,10-dimethoxy-1,2,3,4,6,7-hexahydro-11baH-benzo[a]quinolizine-hydrochloride 3.0 g. (8.64 mmoles) of 2-oxo-3α-(2-methoxycarbonyl-ethyl)-9,10-dimethoxy-1,2,3,4,6,7-hexahydro-11baH-benzo[a]quinolizine is suspended in 50 ml of absolute methanol and after cooling to 0° C., 220 mg. of sodium borohydride is added within 15 minutes. After adding the total amount of the reducing agent the reaction mixture is stirred for 30 minutes. After working up the mixture by a method known per se, the residue is taken up in methanol, and methanolic hydrochloric acid solution is added. 2.0 g. (60%) of hydrochloride salt of the title compound is precipitated.

M.p.: 214°-215° C. The free base is recrystallized from methanol and melts at 115° C.

IR spectrum (KBr): at 3400 (—OH); 2800, 2750 (Bohlmann bands): 1738 (—COOCH₃) cm⁻¹.

Analysis for the formula C₁₉H₂₇NO₅ (molecular weight: 349.40): calculated: C %: 65.35; H %: 7.80; N %: 4.02; found: C %: 65.30; H %: 7.87; N %: 3.94.

Mass spectrum (M/e,%): 349 (M⁺, 23); 348 (85); 347 (99); 303 (75); 231 (43); 204 (100); 190 (96).

EXAMPLE 8

2α-Hydroxy-3α-(2-methoxycarbonyl-ethyl)-9,10-dimethoxy-1,2,3,4,6,7-hexahydro-11baH-benzo[a]quinolizine The mother liquor obtained after the separation of the 2β-hydroxy derivative according to the Example 7. is concentrated in vacuum and the residue is extracted with dichloromethane after alkalizing with sodium carbonate. The water is removed from the organic layer with anhydrous magnesium sulfate and the residue is evaporated. 0.8 g. of solid is obtained which is purified by preparative thin layer chromatography (developed with a 14:3 mixture of benzene methanol) and 300 mg. (10%) of the title compound is obtained. The $R_f$ value of the 2β-derivative is greater than that of the 2α-derivative.

M.p.: 121° C.

IR spectrum (KBr): at 3450 (—OH); 2760 (Bohlmann band); 1742 (—COOCH₃) cm⁻¹.

EXAMPLE 9

2β-Acetoxy-3α-(2-methoxycarbonyl-ethyl)-9,10-dimethoxy-1,2,3,4,6,7-hexahydro-11baH-benzo[a]quinolizine 3.8 g. of the crude product obtained according to Example 7. is dissolved in 64 ml. of a 1:1 mixture of pyridine and acetic acid anhydride and the mixture is allowed to stand for 24 hours at room temperature. The mixture is then under cooling poured on icy water and the pH of the mixture is adjusted to 8 by adding saturated ammonium hydroxide solution. The precipitated substance is filtered and recrystallized from methanol. 1.58 g. of the title compound is obtained. The yield related to the 2-oxo compound is 35%.

M.p.: 125° C. The hydrochloride salt melts at 238°–239° C.

Analysis for the formula $C_{21}H_{29}NO_6$ (molecular weight: 319.46): calculated: C %: 64.43; H %: 7.46; N %: 3.57; found: C %: 64.70; H %: 7.28; N %: 3.88.

IR spectrum (KBr): at 2750 (Bohlmann band);

1730 /—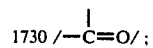=O/;

1220 (C—O—C) cm⁻¹.

Mass spectrum (M/e,%): 391 (17); 390 (51); 389 (32); 331 (100); 303 (43); 204 (35).

EXAMPLE 10

2β-Hydroxy-3α-(2-methoxycarbonyl-ethyl)-9,10-diethoxy-1,2,3,4,6,7-hexahydro-11baH-benzo[a]quinolizine-hydrochloride 2.2 g. (5.94 mmoles) of 2-oxo-3α-(2-methoxycarbonylethyl)-9,10-diethoxy-1,2,3,4,6,7-hexahydro-11baH-benzo[a]quinolizine is suspended in 40 ml. of absolute methanol. The mixture is cooled to 0° C. and 170 mg. (5.96 mmoles) of sodium borohydride is added within 15 minutes under stirring. The reaction mixture is then stirred for a further 20 minutes. The reaction mixture is further treated as described in the previous Examples. The crude oil obtained as a residue is taken up in methanol and the pH is adjusted to 5 with a methanolhydrochloric acid solution. The precipitated hydrochloride salt of the title compound is filtered. Yield: 1.4 g. (58%).

M.p.: 178°–179° C.

Analysis for the formula $C_{21}H_{31}NO_5 \cdot HCl$ (molecular weight: 378.56+36.46): calculated: C %: 60.85; H %: 7.78; N %: 3.48; found: C %: 60.90; H %: 7.82; N %: 3.62.

IR spectrum (KBr): at 3400 (—OH); 1740 (—COOCH₃); 1620 (aromatic system) cm⁻¹.

EXAMPLE 11

2β-Acetoxy-3α-(2-methoxycarbonyl-ethyl)-9,10-diethoxy-1,2,3,4,6,7-hexahydro-11baH-benzo[a]quinolizine 3.8 g. of oily, crude 2β-hydroxy derivative prepared according to Example 10. is taken up in 46 ml. of a 1:1 mixture of pyridine and acetic acid anhydride and the reaction mixture is allowed to stand at room temperature for 24 hours. The mixture is then concentrated in vacuum and icy water is added under cooling. The pH of the obtained mixture is adjusted to 8 with saturated ammonium hydroxide solution. The precipitated solid is filtered and recrystallized from methanol. 1.41 g. (31.1%) of the title compound is obtained. (The yield related to the 2-oxo compound amounts to 31.1%).

M.p.: 104°–105° C. The hydrochloride salt melts at 222°–223° C.

Analysis for the formula $C_{23}H_{33}NO_6$ (molecular weight: 419.51): calculated: C %: 65.85; H %: 7.92; N %: 3.33; found: C %: 65.77; H %: 8.00; N %: 3.54.

IR spectrum (KBr): at 2860, 2750 (Bohlmann bands);

1730 (—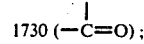=O);

1230 (C—O—C) cm⁻¹.

Mass spectrum (M)e,%): 418 (M⁺, 57); 359 (100); 332 (46); 233 (36).

EXAMPLE 12

2β-Hydroxy- and 2β-hydroxy-3β-(2-cyanoethyl)-9,10-methylenedioxy-1,2,3,4,6,7-hexahydro-11baH-benzo[a]quinolizine 1.0 g. (3.35 mmoles) of 2-oxo-3β-(2-cyanoethyl)-9,10-methylenedioxy-1,2,3,4,6,7-hexahydro-11baH-benzo[a]quinolizine is stirred in 15 ml. of methanol and 0.153 g. (4.00 mmoles) of sodium borohydride is added to the system stirred with a magnetic stirrer at 0° C. The reaction mixture is then further stirred for 30 minutes at 0° C., the precipitated crystalline substance is filtered and washed with water. 0.453 g. of the title compound is obtained. 2 drops of glacial acetic acid is added to the methanolic solution, evaporated to dryness and the residue is triturated with 2.5% sodium bicarbonate solution and the aqueous solution is shaken with dichloromethane. This solution is dried with anhydrous magnesium sulfate, evaporated to dryness and the residue is recrystallized from methanol. Thus another 0.232 g. of 2β-hydroxy compound of the title compound is obtained.

The methanolic mother liquor is separated on a preparative thin layer chromatography plate KG-PF₂₅₄₋₃₆₆.

A total amount of 0.453+0.232+0.111 g. (from the plate)=0.796 g. (79%) of 2β-hydroxy compound is obtained. $R_f$=0.29 (developed with a 14:3 benzene:methanol mixture).

M.p. 185°–186° C.

IR spectrum (KBr): at 3510 (—OH); 2360 (—CN) cm⁻¹.

Analysis for the formula $C_{17}H_{20}N_2O_3$ (molecular weight: 300.35): calculated: C %: 67.97; H %: 6.71; found: C %: 67.99; H %: 6.70.

Mass spectrum (M)e,%): M+ 300 (85.1); 299 (100); 283 (24.3); 256 (56.9); 216 (78.1); 189 (63.2); 175 (67.2); 174 (32.1).

NMR spectrum in deutero-chloroform: at $\delta = 5.88$ (2H, s, —O—CH$_2$—O—); 6.54; 6.61 (2H, s, aromatic protons) ppm.

A total amount of 0.091 g. (9.0%) of the 2α-hydroxy derivative of the title compound is obtained. $R_f = 0.27$ (KG-G plate, developed with a 14:3 mixture of benzene methanol).

M.p.: 136°–138° C.

Analysis for the formula $C_{17}H_{20}N_2O_3$ (molecular weight: 300.35): calculated: C %: 67.97; H %: 6.71; found: C%: 67.91; H %: 6.70.

IR spectrum (KBr): at 3100–3500 (—OH); 2360 (—CN) cm$^{-1}$.

NMR spectrum (in deutero-chloroform): at $\delta = 5.76$ (2H, s, —O—CH$_2$—O—); 6.41, 6.49 (2H, 2s, aromatic protons) ppm.

What we claim is:

1. A compound of the formula I or an acid addition salt thereof

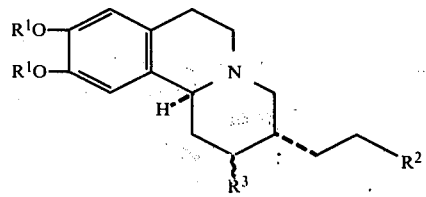

wherein
R$^1$ is C$_{1-4}$ alkyl or form together a methylene bridge,
R$^2$ is cyano, or an alkoxycarbonyl group having a C$_{1-4}$ alkyl group in the alkoxy portion,
R$^3$ is hydroxy or alkanoyloxy having a C$_{1-4}$ alkyl in the alkoxy portion in α- or β-steric position.

2. A compound as defined in claim 1, wherein
R$^1$ is a methyl or ethyl group or forms together a methylene bridge,
R$^2$ is cyano or methoxycarbonyl,
R$^3$ is hydroxy or acetoxy in α- or β-position, or a hydrochloride thereof.

3. A compound selected from the group which consists of:
2α-hydroxy-3α-(2-cyanoethyl)-9,10-dimethoxy-2α-hydroxy-3α-(2-cyanoethyl)-9,10-diethoxy-, and 2α-hydroxy-3α-(2-cyanoethyl)-9,10-methylenedioxy-1,2,3,4,6,7-hexahydro-11bαH-benzo[a]-quinolizine hydrochlorides.

4. An antiinflammatory, analgesic and gastric juice secretion inhibiting pharmaceutical composition which comprises as active ingredient an effective amount at least one compound of formula I as defined in claim 1 and the pharmaceutically acceptable acid addition salts thereof mixed with pharmaceutically acceptable carriers.

5. A process for treatment to obtain antiinflammatory, analgesic and gastric juice secretion inhibiting pharmaceutical effects which comprises administering effective amounts of at least one of the compounds of formula I as defined in claim 1, in a pharmaceutically acceptable carrier.

* * * * *